United States Patent [19]

Persyk

[11] Patent Number: 4,523,091
[45] Date of Patent: Jun. 11, 1985

[54] RADIATION DETECTING APPARATUS WITH REDUCED MAGNETIC FIELD SENSITIVITY

[75] Inventor: Dennis E. Persyk, Barrington, Ill.

[73] Assignee: Siemens Gammasonics, Inc., Des Plaines, Ill.

[21] Appl. No.: 360,338

[22] Filed: Mar. 22, 1982

[51] Int. Cl.³ .............................................. H01J 31/50
[52] U.S. Cl. ........................... 250/213 VT; 250/363 S; 313/532
[58] Field of Search ............. 250/213 VT, 363 S, 239; 313/532; 315/8

[56] References Cited

U.S. PATENT DOCUMENTS

| | | | |
|---|---|---|---|
| 3,809,889 | 5/1974 | McBroom | 250/213 VT |
| 4,220,890 | 9/1980 | Beekmans | 250/213 VT X |
| 4,221,967 | 9/1980 | Wang et al. | 250/213 VT X |
| 4,328,418 | 5/1982 | Morgan et al. | 250/213 VT |

Primary Examiner—Edward P. Westin

[57] ABSTRACT

The radiation detecting apparatus contains at least one photomultiplier tube for the detection of light. It has been found that the photomultiplier tube will emit erroneous output signals when exposed to a perturbing magnetic field. This is particularly true for photomultiplier tubes used in scintillation cameras and in emission computed tomography systems where the detector head containing photomultipliers changes position during operation. In order to reduce the magnetic field sensitivity, the radiation detection apparatus contains means for superimposing an artificial magnetic field on the perturbing magnetic field at the location of the photomultiplier tube. This artificial field may either be a compensating field or, preferably, an enhancing field which is larger than the perturbing field. The artificial field may be either generated by coils, such as Helmholtz coils, or by a permanent magnet. The coil(s) may be arranged inside or outside the camera head.

10 Claims, 10 Drawing Figures

RADIATION DETECTING APPARATUS WITH REDUCED MAGNETIC FIELD SENSITIVITY

BACKGROUND OF THE INVENTION

1. Field of the Invention This invention relates to a radiation detection apparatus which contains at least one photomultiplier tube for the detection of light. In particular, this invention relates to a radiation detection apparatus such as a detector head for a gamma scintillation camera or a radionuclide emission computed tomography system.

2. Description of the Prior Art Photomultiplier tubes are widely used in radiation detecting apparatus such as a gamma radiation scintillation camera (see e.g. U.S. Pat. No. 3,011,057 Anger) and in both positron emission computed tomography or in positron ECT, (see e.g. IEEE Transactions on Nuclear Science, Vol.NS-23, February 1976, pp. 528–537) and single photon emission computed tomography, or SPECT (see e.g. IEEE Transactions on Nuclear Science, Vol. NS-28, February 1981, pp. 69–80). This invention applies to all such radiation detectors. For brevity, the term ECT subsequently is used for both SPECT and positron ECT systems.

It has been observed that the sensitivity of a photomultiplier tube varies with the position of the tube with respect to room coordinates. In particular, it has been realized that the sensitivity of a photomultiplier tube is a function of its orientation with regard to the magnetic field of the earth. Examinations also have proved that some types of photomultiplier tubes typically used for gamma camera applications are sensitive to magnetic fields of the order of 1Gauss ($10^{-4}$ Tesla).

As far as photomultiplier tubes are concerned which are incorporated in a conventional scintillation camera, no specific measures have been taken to compensate for the influence of the earth's magnetic field. The reason herefor is that a change of the camera orientation does not have any immediate impact on the quality of the camera image. In a conventional stationary camera the magnetic field orientation does not change in any way while images are taken, and in a conventional scanning camera the orientation of the camera head with respect to the earth's magnetic field is not altered during a scanning operation of the head.

In the case of a single head SPECT system, a single camera head rotates about the patient to be examined. In a dual SPECT system or positron ECT system, two opposing camera heads rotate about the patient. In both types of ECT systems, an influence can be observed which is periodic with the rotation. It has been found that this influence is caused by the sensitivity of the incorporated photomultiplier tubes to the varying orientation with respect to the earth's magnetic field. The periodic perturbation of the tube sensitivity may cause artifacts in the reconstructed ECT images. These magnetic field induced artifacts may impede the analysis of patient images.

In new types of stationary cameras, and in ECT camera systems, manufacturers have designed sophisticated correction techniques correcting for linearity (that is, the LC part in a so-called ZLC camera), flood uniformity, and/or spatial energy variations (that is, the Z part in a ZLC camera).

Most of these techniques require the acquisition of a correction matrix, that is the acquisition of an XY-two dimensional representation of the amount of correction that has to be made. If the camera is operated in a position different from the position in which the correction matrix was established, image distortions or non-uniformity effects may occur, since the magnetic field in the operating position may be different.

Magnetic shielding may reduce magnetic field effects to a certain degree. However, shielding is usually not inexpensive because it involves shielding material which is costly and which requires some labor to be formed into special shapes. In general, very carefully designed shielding will be needed. It will be noted however, that it is difficult to shield adequately against axial fields, that is magnetic fields parallel to the photomultiplier axes. These axes are conventionally parallel to the axis defined by the collimator. In some cases, such on-axis shielding is not even possible, or it produces undesirable effects. In conventional gamma cameras, no shielding is used on the scintillator, with the exception of that provided by the collimator.

Another approach to overcome magnetic field problems would be to position the scintillation camera or the ECT camera in a shielded room or within the volume of large Helmholtz coils. This, of course, is also an expensive solution. Such Helmholtz coils could not compensate for field distortions produced by other smaller sources such as an electric motor, a solenoid actuator, or a transformer. As the field of view is increased in gamma cameras and ECT procedures become more refined, magnetic field effects will become more troublesome. Therefore, it seems advisable to find solutions which reduce these problems.

SUMMARY OF THE INVENTION

1. Objects

It is an object of this invention to provide a radiation detecting apparatus incorporating at least one photomultiplier tube for the detection of light, which apparatus has a reduced sensitivity with respect to perturbing magnetic fields.

It is another object of this invention to provide a scintillation camera wherein the magnitude of distortions and/or non-uniformity effects due to perturbing magnetic fields is effectively reduced in a comparatively inexpensive way.

It is still another object of this invention to provide an ECT system wherein artifacts in the reconstructed ECT images caused by perturbing magnetic fields are substantially reduced in a comparatively inexpensive way.

It is still another object of this invention to provide a radiation detecting apparatus the operation of which is virtually unaffected by the earth's magnetic field.

2. Summary

According to this invention, a radiation detection apparatus contains at least one photomultiplier tube for the detection of light, whereby this photomultiplier tube may be exposed to a perturbing magnetic field. The radiation detection apparatus also contains means for superimposing an artificial magnetic field on said perturbing magnetic field at the location of the photomultiplier tube.

The means for superimposing an artificial magnetic field may be a permanent magnet. Alternatively, this means may contain at least one magnetic coil and a current source for passing an electric current through the coil. In particular, two coils may be provided in Helmholtz arrangement. If desired the magnet or coil arrangement may be such that it produces a magnetic field which extends along the longitudinal axis of the photomuliplier tube.

According to one embodiment of the invention, the artificial magnetic field may be such that it reduces or even compensates the perturbing magnetic field. According to another embodiment, however, the artificial magnetic field is directed such that it enhances the perturbing magnetic field.

For this latter purpose, it is necessary that the artificial magnetic field has approximately the same direction as the perturbing magnetic field. The strength of the artificial magnetic field should be greater than the strength of the perturbing magnetic field. In some cases the strength of the artificial field may be selected much greater than the strength of the perturbing field, for instance 10 times or more.

Reduction of the magnetic field sensitivity of photomultiplier tubes is especially important in detector heads of gamma ray scintillation cameras and of ECT systems. Thus, the invention applies to single-head SPECT systems, to dual-head SPECT systems, to positron ECT cameras, and to conventional-head gamma cameras.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
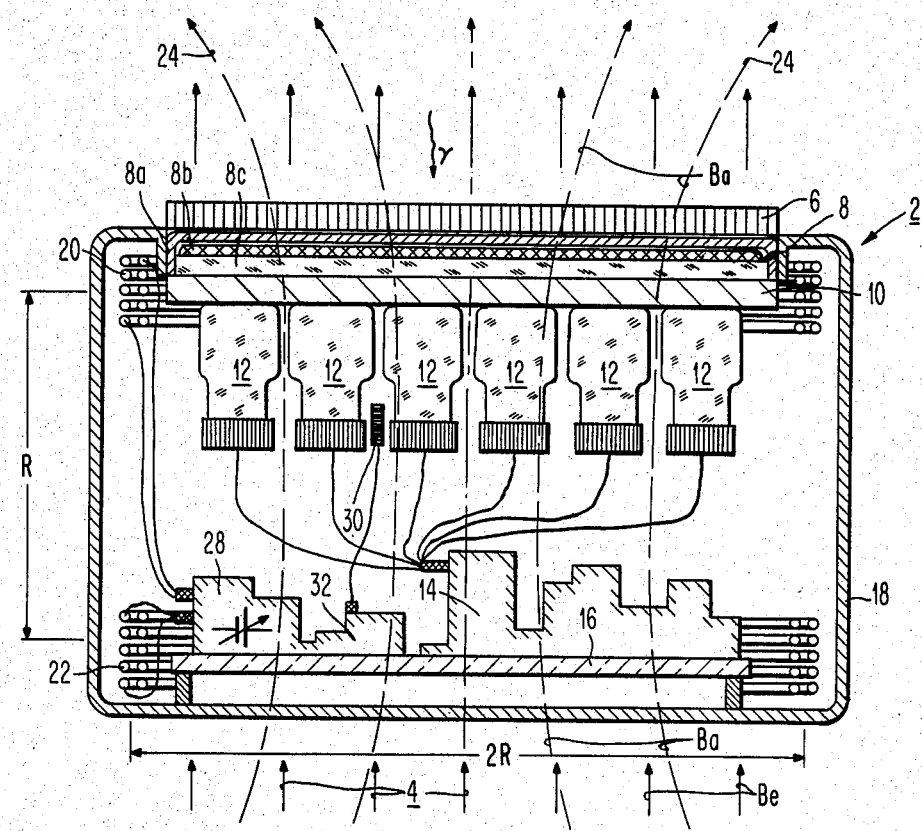
FIG. 1 is a schematic view of a cross section of a scintillation camera head incorporating two magnetic coils for generating an enhancing magnetic field at the location of the photomultipliers, according to the present invention.

With reference to FIG. 1, a scintillation camera head 2 is illustrated which is exposed to an external magnetic field 4 having the strength $B_e$, such as the earth's magnetic field. The camera head 2 may be the head of a stationary gamma camera or of an ECT system. It contains a collimator 6 which comprises a plurality of parallel radiation channels. The camera head 2 also contains an encapsulated scintillation crystal assembly 8 of conventional design. The assembly 8 comprises a gamma entrance window 8a, for instance of a metal such as aluminum, a scintillator crystal 8b, and a cover plate 8c, for instance of pyrex or glass.

Impinging gamma rays generate scintillation light flashes in the crystal assembly 8. A light guide or light pipe 10 which can be part of the scintillation crystal assembly 8 guides the light to a number of photomultiplier tubes 12. These photomultiplier tubes 12 are arranged, for instance, in a hexagonal pattern. Their longitudinal axes are parallel to each other and parallel to the field lines of the magnetic field 4. These photomultiplier tubes 12 serve to detect the scintillation light generated in the scintillation crystal 8.

The outputs of the photomultiplier tubes 12 are connected to electronic evaluation circuitry 14, the silhouette of which is shown in FIG. 1. This circuitry 14 is mounted on a board 16 which is attached to a conventional head housing 18 of cylindrical shape. The housing 18 serves to hold the various parts 8 to 16 and to provide magnetic and radiation shielding. The housing 18 may be made, for instance, of cast iron.

It will be noted that the longitudinal axes of the photomultiplier tubes 12 are arranged parallel to the cylinder axis of the housing 18. In the embodiment shown in FIG. 1, it is assumed that the field lines of the perturbing magnetic field 4 are parallel to the housing axis.

Inside the housing 18, there are provided a first electric coil 20 and a second electric coil 22 in Helmholtz arrangement. That is, the radius R of each coil 20, 22 equals the distance R of the coils 20, 22 from each other. When energized, the Helmholtz coils 20, 22 generate a magnetic field 24 of the strength $B_a$ which is homogeneous within the volume comprised by the coils 20, 22, that is, in the region of the tubes 12. In other words, the magnetic field lines of the artificial field 24 are virtually parallel to the axis of the cylindrical housing 18. Thus, the field lines due to the Helmholtz coil pair 20, 22 are on-axis with respect to the longitudinal axes of the photomultipliers 12.

The coils 20, 22 are energized by an energy source 28 of variable strength which source 28 is also supported by the board 16. In the illustrated embodiment the coils 20, 22 receive a current such that the resulting artificial field 24 enhances the perturbing magnetic field 4 in the region of the photomultiplier tubes 12.

A very sensitive magnetic field sensor 30 is located in the region of the photomultipliers 12. The sensor 30 may be a Hall detector which is commercially available. This sensor 30 senses the magnetic field 4 and field changes, for instance, in the order of 1/100 Gauss ($10^{-6}$ Tesla) The output signal of the sensor 30 provides a warning that magnetic field perturbations may compromise the imaging quality of the gamma camera. The output signal of the sensor 30 is fed into a control circuit 32 which controls the current source 28, therby controlling the current flowing through the coils 20 and 22.

In the embodiment of FIG. 1, the electromagnetic coils 20, 22 have the function of providing a swamping magnetic field 24, that is a strong field in the same direction as the external perturbing field 4. The intensity $B_e$ of this swamping magnetic field 24 is far greater than the intensity $B_e$ of the external perturbing field 4. Since the resulting field in the region of the photomultipliers 12 is large and in the order of magnitude of the artificial field 24, a change of the perturbing field 4 due to a change of the camera head position with respect to the field 4 does not cause any significant field change at the location of the photomultiplier tubes 12. Therefore, the camera head 2 does not exhibit undesirably large magnetic field sensitivity effects.

Figure 2:
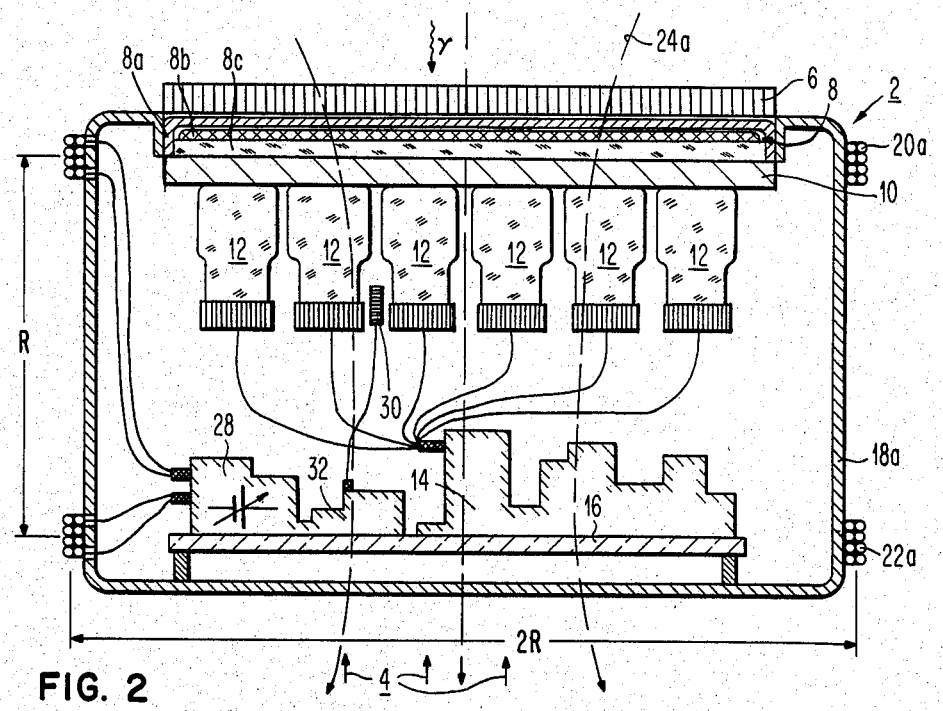
FIG. 2 is another embodiment of this invention similar to the embodiment of FIG. 1, whereby a pair of coils is arranged on the outside of a scintillation camera.

In FIG. 2, an embodiment of a camera head 2 is illustrated which is similar to the embodiment of FIG. 1. Here the first and second magnetic coils 20a and 22a are arranged on the outside wall of the housing 18. Again, a Helmholtz arrangement is selected. In this case, the housing 18a is permeable to the magnetic field 24a generated by the coils 20a, 22a. In this embodiment, the electromagnetic coils 20a, 22a are supplied such as to serve another function as in FIG. 1. They provide the magnetic field 24a in the region of the photomultiplier tubes 12 as a correction or compensating field. In this embodiment, the current source 28 causes currents to flow through the coils 20a, 22a in such a manner as to minimize the total field. This total field may again be sensed by a sensor 30 which is connected to control circuitry 32. The circuitry 32 in turn controls the output of the source 28 such that the total field sensed by the sensor 30 is minimized. A change of the position of the camera head 2 with respect to the perturbing field 4 is sensed by the sensor 30 as a change of the total field. As a result, the control circuit 32 alters and corrects the currents flowing through coils 20a, 22a so as to minimize the total field at the new location of the photomultiplier tubes 12. Thus, the magnetic field sensitivity of the camera head 2 is compensated for.

Of course, such a compensating field 24a may also be generated by Helmholtz coils arranged within the housing 18, as in FIG. 1.

Instead of a single sensor 30, several sensors may be positioned in the region of the photomultiplier tubes 12.

With respect to FIG. 1 it has been mentioned that the coils 20, 22 together represent a Helmholtz coil pair. The magnetic field 24 within the volume of these coils 20, 22 is nearly uniform, with the best uniformity being, obtained in the more inward volume of the region. Thus, the coils 20, 22 in FIG. 1 are arranged to produce as uniform a magnetic field 24 as possible in the volume containing the photomultiplier tubes 12, which volume is but a small portion of the total volume enclosed by the coils 20, 22.

It should be noted with respect to FIGS. 1 and 2, that depending on the material the housing 18, 18a may distort the magnetic field produced by the coils 20, 22 and 20a, 22a. However, a uniform field 24, 24a is not necessarily required. Rather, the magnetic field 24 produced by the coils 20, 22 must either swamp the external field 4, as in FIG. 1, or the magnetic field 24a must correct the effect of the external field 4, as in FIG. 2. For this purpose, the generated field 24 or 24a does not need to be uniform.

It is to be noted also that because the swamping field 24 or the correction field 24a is comparatively weak and need not be uniform, the coils may be located outside the camera housing 18a, as shown in FIG. 2. This allows retrofitting to cameras not initially incorporating means for compensating magnetic field sensitivity effects. This also can save space inside the housing 18a.

It should also be pointed out that in some cases a single internal or external coil would suffice, and that other cases may require an external coil plus an internal coil.

In terms of the magnitude of the applied fields 24 and 24a, the following has been found: the swamping field 24 may be of the order of a few Gauss, that is between 1 and 10 Gauss, while the correction field 24a may be of similar strength, depending on the nature of the external perturbing field 4. Such a perturbing field 4 may be, for instance, the earth's field, a motor field, a solenoid field, an AC line field, etc.

It has already been mentioned that in the preferred embodiment the sensor 30 is located within the housing 18, 18a, preferably near the center of the array of photomultiplier tubes 12. However, several sensors may be located around the periphery of the housing 18, 18a, that is external to the housing 18, 18a. This would be advantageous for retrofitting.

The advantage of a compensating field 24a as shown in FIG. 2 is best present when the perturbing magnetic field 4 is aligned within approximately 20° to 30° of the common axis of the Helmholtz coils 20a, 22a. Two pairs of Helmholtz coils would be needed to take care of all the orientations of the camera head 2 in the compensating field method according to FIG. 2.

Figure 3:
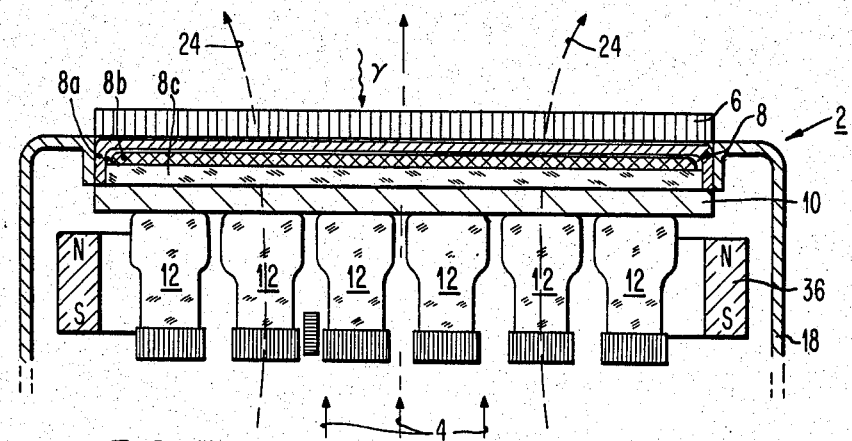
FIG. 3 is a partial cross section of a scintillation camera wherein a permanent magnet is used, according to this invention.

With reference to FIG. 3, the interior of the camera head 2 of a scintillation camera may contain a permanent magnet 36 for generating a swamping field 24 in the region of the photomultiplier tubes 12. The permanent magnet 36 is provided as a ring surrounding the array of photomultiplier tubes 12. Such annular magnets 36 which are flexible are commercially available.

Figure 4:
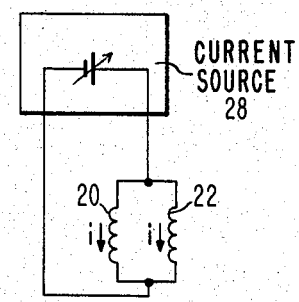
FIG. 4 is a circuit diagram illustrating a current source energizing two magnetic coils, which generate an enhancing field, according to this invention.

FIG. 4 illustrates a simple circuit diagram including any conventional adjustable current source 28 for energizing the Helmholtz coils 20, 22. The coils 20, 22 may be connected parallel to each other. The arrow in the current source 28 represents some adjusting means for adjusting the currents i flowing through the coils 20, 22. The illustrated circuitry may be used in the embodiment of FIG. 1 for providing a swamping field 24. Thus, the currents i are adjusted such that the magnetic field 24 is either much larger or slightly larger than the perturbing magnetic field 4.

Figure 5:
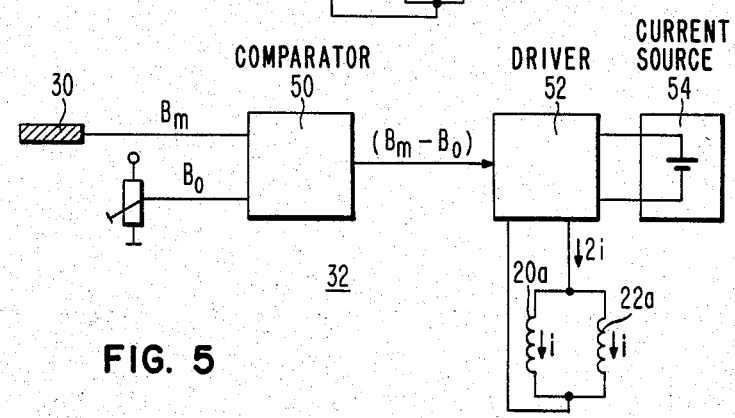
FIG. 5 is a circuit diagram of a control circuit for energizing two magnetic coils which generate a compensation field, according to this invention.

In FIG. 5 a control circuit 32 for controlling the current i in two compensating coils 20a, 22a (see FIG. 2) is illustrated. The output signal $B_m$ of the magnetic sensor 30 is fed into a comparator 50. The signal $B_m$ is an indication of the total field at the location of the sensor 30. This signal $B_m$ is here compared with a preset value $B_o$. This preset value $B_o$ may be, for instance, O. The output signal of the comparator 50 is applied to a driver stage 52 which varies the output voltage of a current source 54 in accordance therewith. The controlled output current $2i$ of the current source 54 is distributed equally among the compensating coils 20a, 22a, which are connected parallel to each other. Thus, the current i flows through each coil 20a, 22a. This current i varies according to the deviation of the measured field $B_m$ from the desired field $B_o$.

Figure 6:
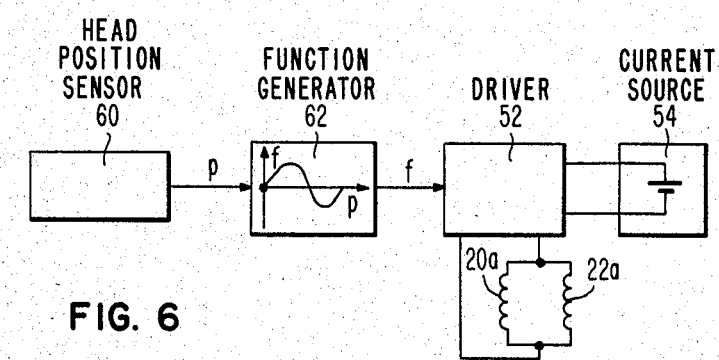
FIG. 6 is another circuit diagram of a control circuit for energizing two magnetic coils according to this invention.

In FIG. 6 another control circuit for two magnetic coils 20a, 22a is illustrated. In this embodiment it is assumed that the camera head is moved with respect to a patient, thereby moving with respect to the perturbing magnetic field of the earth. Once the camera has been installed, each individual position of the camera head is geared to a certain strength and direction of the magnetic field. Thus, the head position is directly a function of the magnetic field strength.

According to FIG. 6, a head position sensor 60 is used. Such a sensor 60 is already installed in many scintillation cameras. The output signal p of the head position sensor 60 is fed into a function generator 62 which contains stored therein a coordination device coordinating the position signal p to the field strength prevailing at any particular location. The output signal f is an indication of the field strength needed to compensate the perturbing field at a particular camera location. This signal f is fed into a driving stage 52 which controls the current 2i flowing from a current source 52 to the coils 20a, 22a.

Figures 7, 8:
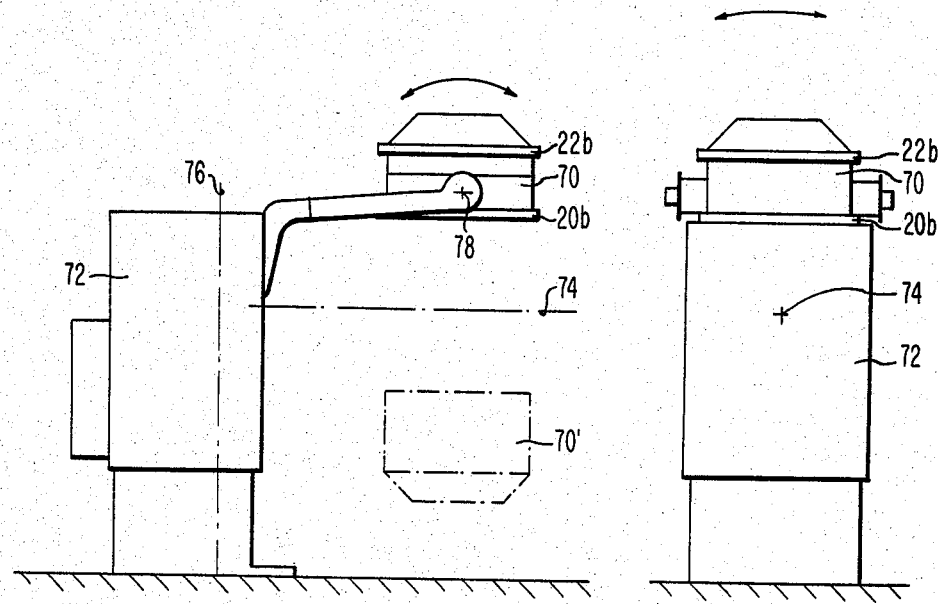
FIG. 7 is a side view of a scintillation camera having a single detector head equipped with field sensitivity compensating means, according to this invention.
FIG. 8 is a front view of the scintillation camera illustrated in FIG. 8.
Figure 9:
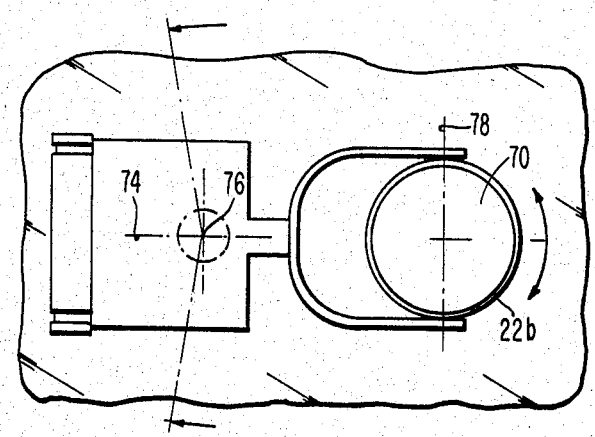
FIG. 9 is a plan view of the scintillation camera illustrated in FIG. 7.

In FIGS. 7 through 9 is illustrated a gamma camera having a single camera head 70. This head 70 can be used for emission computed tomography (ECT) and/or for planar imaging. The head 70 is attached to a stand 72 such that it is rotatable about various rotation axes 74, 76 and 78. In FIG. 7, a head 70' is shown in dotted lines. This is the head 70 rotated by 180° about the horizontal rotation axis 74 with respect to its initial vertical position.

It will be noted that a pair of Helmholtz coils 20b and 22b is provided on the head 70. These coils 20b and 22b have their axes aligned parallel to the head axis. In FIGS. 7 through 9 the Helmholtz coils 20b and 22b are shown to be arranged outside the housing of the head 70. Instead, they may be arranged within the housing itself.

The coil axes are parallel to the axes of the individual photomultiplier tubes which are positioned within the camera head 70.

Figure 10:
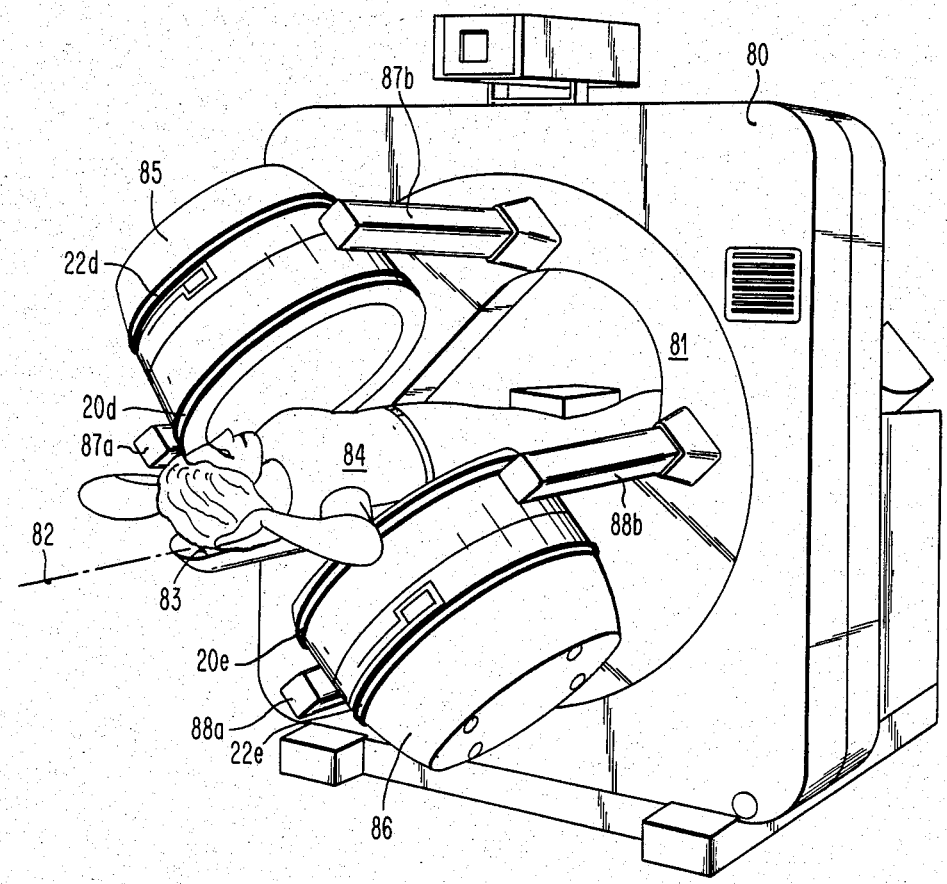
FIG. 10 is a perspective view of a single photon emission computed tomography system according to this invention.

In FIG. 10 is illustrated a versatile gamma imaging system that provides detection capability for single photon emission computed tomography (SPECT) applications and also serves as a conventional gamma camera with or without scanning properties.

The imaging system comprises a frame structure or gantry 80. The central opening of the gantry 80 contains a ring structure 81 which is rotatable about a horizontal axis 82. A table top 83 for carrying a patient 84 extends along the axis 82 through the central opening of the ring 81. Two high-performance detector heads 85 and 86 are accomodated on the camera ring 81 by means of cantilevers 87a, 87b and 88a, 88b, respectively. The camera heads 85 and 86 are preferably ZLC detector heads. In SPECT applications, the dual detector heads 85, 86 double the sensitivity of the system and thus improve image statistics for a given counting rate. Alternately, they can be used in conventional procedures. For SPECT reconstructive imaging, the detector heads 85 and 86 are jointly rotated around the patient 84. The detectors track the center line of rotation precisely as they are rotated around the patient 84. Accurate information regarding the detector position is continuously transmitted for image reconstruction.

The table top 83 is four-way motorized, thereby facilitating patient positioning with cranial, caudial and transverse motions. The patient 84 is positioned in the center of rotation.

Since the gamma imaging system is equipped with dual detector heads 85 and 86, a major advantage results. Dual opposing views, scanned simultaneously, can double patient throughput. For whole body surveys, the system performs dual pass scanning. The motorized table top moves the patient 84 smoothly and accurately between the detector heads 85, 86. Thus, the system fulfills the requirements of a conventional nuclear medicine gamma camera.

In FIG. 10 is shown that each detector head 85 and 86 is provided with a Helmholtz coil pair 20d, 22d and 20e, 22e respectively. These coil pairs are arranged on the outside of the detector heads 85 and 86, respectively. The external coils are used here again to "swamp" the undesired magnetic field of the earth or of another undesired magnetic source. In other words, the magnetic field caused by the Helmholtz coil pairs within the detector heads 85 and 86 is stronger than the perturbing magnetic field. Thus, the photomultiplier tubes contained in the detector heads 85 and 86 are exposed to strong swamping fields so that a change of the undesired external magnetic field does not have any significant influence when the heads 85 and 86 are rotated about the rotation axis 82, thereby changing their position with respect to the direction of the disturbing external magnetic field.

Alternately, the Helmholtz coil pairs 20d, 22d and 20e, 22e can be energized such that they generate a (small) magnetic field which compensates for the perturbing magnetic field of the undesired source. Since the compensating field generated by the coil pairs varies with the rotation about the rotation axis 82, the strength of these fields must be varied accordingly. This can be performed again by a circuit which varies the field strength of the artificial magnetic field in dependence on the position of the heads 85 and 86 with respect to the perturbing magnetic field. Since accurate information regarding the detector position is continuously transmitted for image reconstruction in a SPECT camera anyway, this information can also be used for controlling the field that varies the artificial field strength, als illustrated in FIG. 6.

It should be mentioned that the invention is not restricted to a radiation detecting apparatus employing necessarily photomultiplier tubes, even though photomultiplier tubes are a preferred application. The invention is applicable to any radiation detecting apparatus employing photoemissive devices, such as electron tube devices and microchannel devices, wherein magnetic field effects may cause performance problems. Thus, the term "photomultiplier tube" is used herein in a generic sense comprising all kinds of photoemissive devices.

While the forms of the radiation detecting apparatus herein described constitute preferred embodiments of the invention, it is to be understood that the invention is not limited to these precise forms of assembly, and that a variety of changes may be made therein without departing from the scope of the invention.

What is claimed is:

1. A radiation detection apparatus containing
   (a) at least one photomultiplier tube for the detection of light, said photomultiplier tube being exposed to a perturbing magnetic field; and
   (b) means for superimposing an artificial magnetic field on said perturbing magnetic field at the location of said photomultiplier tube wherein the strength of said artificial magnetic field is greater than the strength of said perturbing magnetic field, such that a change of said perturbing magnetic field due to a change of the position of said photomultiplier tube does not cause any significant field change at the location of said photomultiplier tube.

2. The apparatus according to claim 1, wherein said means for superimposing an artificial magnetic field is a permanent magnet.

3. The apparatus according to claim 1, wherein said means for superimposing an artificial magnetic field comprises at least one magnetic coil and means for passing an electric current therethrough.

4. The apparatus according to claim 3, wherein two coils are provided in Helmholtz arrangement.

5. The apparatus according to claim 1, wherein said artificial magnetic field extends along the longitudinal axis of said photomultiplier tube.

6. The apparatus according to claim 3, wherein means are provided for controlling said electric current, said control means including a sensor for sensing said perturbing magnetic field.

7. The apparatus according to claim 1, wherein the strength of said artificial magnetic field is 10 times or more the strength of said perturbing magnetic field.

8. The apparatus according to claim 1, wherein a plurality of photomultipliers are provided for detecting light from a scintillation crystal, wherein said photomultipliers are arranged parallel to each other, and wherein said artificial magnetic field extends along the longitudinal axes of said photomultiplier tubes.

9. The apparatus according to claim 8, wherein said photomultiplier tubes are arranged within a housing, wherein said means for superimposing an artificial magnetic field comprises at least one electric coil, and wherein said coil is also arranged within said housing.

10. The apparatus according to claim 8, wherein said photomultiplier tubes are arranged within a housing, wherein said means for superimposing an artificial magnetic field comprises at least one electric coil, and wherein said coil is arranged outside said housing.

* * * * *